United States Patent
Thorne et al.

(10) Patent No.: US 9,417,166 B2
(45) Date of Patent: Aug. 16, 2016

(54) SYSTEM AND METHOD FOR INCREASED COOLING RATES IN RAPID COOLING OF SMALL BIOLOGICAL SAMPLES

(75) Inventors: Robert E. Thorne, Ithaca, NY (US); Matthew W. Warkentin, Brooktondale, NY (US); Viatcheslav Berejnov, Victoria (CA)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 12/239,304

(22) Filed: Sep. 26, 2008

(65) Prior Publication Data

US 2009/0133410 A1    May 28, 2009

Related U.S. Application Data

(63) Continuation of application No. PCT/US2007/007963, filed on Mar. 30, 2007.

(60) Provisional application No. 60/787,206, filed on Mar. 30, 2006, provisional application No. 60/847,666, filed on Sep. 28, 2006.

(51) Int. Cl.
*F25D 17/02* (2006.01)
*G01N 1/42* (2006.01)
*A01N 1/02* (2006.01)

(52) U.S. Cl.
CPC .. *G01N 1/42* (2013.01); *A01N 1/02* (2013.01); *A01N 1/0242* (2013.01); *A01N 1/0257* (2013.01); *A01N 1/0268* (2013.01)

(58) Field of Classification Search
CPC ..... A01N 1/02; A01N 1/0278; A01N 1/0257; A01N 1/42; A01N 1/0268; A01N 1/0242; F25D 23/10; F25D 3/11; F25D 3/105; F25D 2400/30; F25D 3/107; F25C 1/00; F25C 1/12; G01N 1/00; G01N 7/00
USPC .............. 62/62, 63, 52.164, 66, 74, 293, 347; 435/1.3, 2, 307.1
See application file for complete search history.

(56) References Cited

U.S. PATENT DOCUMENTS

| | | | | |
|---|---|---|---|---|
| 3,413,818 A | * | 12/1968 | Pelmulder | 62/63 |
| 4,485,641 A | * | 12/1984 | Angelier et al. | 62/51.1 |
| 4,559,298 A | * | 12/1985 | Fahy | A01N 1/02 435/1.2 |

(Continued)

OTHER PUBLICATIONS

Linda J. Walker, et al., "Cryocrystallography: effect of cooling medium on sample cooling rate," J. Appl. Cryst., vol. 31, pp. 954-956 (1998).

*Primary Examiner* — Emmanuel Duke
(74) *Attorney, Agent, or Firm* — William Greener; Bond, Schoeneck & King, PLLC

(57) ABSTRACT

A method and devices for rapid cooling of small biological samples by plunging them in a cryogenic liquid, such as liquid nitrogen, or contacting them with a cryogenic metal surface, reduce or eliminate the cold gas layer that forms above the liquid cryogens or cryogenic surfaces, producing an abrupt transition from ambient (e.g., room) temperature to the cryogen temperature as the sample enters the liquid or contacts the surface. To reduce or eliminate the effects of the cold gas layer, a flow of warm dry gas can be directed along the plunge path, for example. By removing this cold gas layer, cooling times for a 10 micron sample (the size of single cells and the smallest protein crystals now used protein crystallography) will decrease to ~0.001 s.

22 Claims, 9 Drawing Sheets

(56) References Cited

U.S. PATENT DOCUMENTS

| | | | |
|---|---|---|---|
| 4,704,873 A | 11/1987 | Imaike | |
| 4,707,998 A * | 11/1987 | Linner | B01D 8/00 118/50.1 |
| 4,723,420 A * | 2/1988 | Sitte | 62/51.1 |
| 4,745,764 A * | 5/1988 | Sitte | G01N 1/42 62/51.1 |
| 4,751,828 A * | 6/1988 | Coulter et al. | 62/51.1 |
| 4,807,442 A * | 2/1989 | Linner | B01D 8/00 118/50.1 |
| 4,888,956 A * | 12/1989 | le Roux Murray | 62/51.1 |
| 5,044,165 A * | 9/1991 | Linner | B01D 8/00 118/50.1 |
| 5,475,984 A * | 12/1995 | Fermani | B01J 2/06 62/373 |
| 5,644,922 A * | 7/1997 | Linden | G01N 1/42 62/51.1 |
| 5,715,686 A | 2/1998 | Arav | |
| 5,873,254 A | 2/1999 | Arav | |
| 6,381,967 B1 * | 5/2002 | Craig | 62/64 |
| 6,528,309 B2 | 3/2003 | Levine | |
| 6,640,576 B2 * | 11/2003 | Berghoff et al. | 62/380 |
| 6,702,523 B1 | 3/2004 | Docheff, III | |
| 6,862,890 B2 | 3/2005 | Williams, III | |
| 7,293,426 B2 * | 11/2007 | Heuser | A01N 1/00 62/373 |
| 7,353,657 B2 | 4/2008 | Craig | |
| 2008/0075777 A1 * | 3/2008 | Kennedy | B01D 9/0027 424/484 |
| 2010/0216230 A1 * | 8/2010 | Thorne | A01N 1/02 435/307.1 |

* cited by examiner

SYSTEM AND METHOD FOR INCREASED COOLING RATES IN RAPID COOLING OF SMALL BIOLOGICAL SAMPLES

CROSS REFERENCE TO RELATED APPLICATIONS

This application is a continuation under 35 U.S.C. 120 and 365(c) of International Application No. PCT/US07/07963, which was filed on Mar. 30, 2007, designates the U.S. and claims the benefit under 35 U.S.C. 119(e) of U.S. Application Nos. 60/787,206, filed Mar. 30, 2006, and 60/847,666, filed Sep. 28, 2006, which are hereby incorporated by reference.

BACKGROUND OF THE INVENTION

1. Field of the Invention

The present invention relates in general to a method and devices for rapid cooling of small (10 microliter or smaller) biological samples to cryogenic temperatures (approximately 150 K or less). The method and devices minimize the thickness of the cold gas layer that forms above the surfaces of liquids and solids (e.g., copper) cooled to cryogenic temperatures, replacing this cold gas layer with gas at another, warmer and more uniform temperature at the same or similar pressure.

2. Description of the Background Art

Cryopreservation of proteins, cells, tissues and other biological samples plays an important role in modern biology and medicine. For example, proteins extracted from natural sources or obtained from genetically engineered organisms and dissolved in an aqueous (water-containing) buffer are often frozen in liquid nitrogen at its boiling or vaporization temperature $T_v=77$ K and then stored in liquid nitrogen, in dry ice ($T_v=195$ K) or cryogenic freezers ($T\approx 195$ K) to prevent them from degrading. However, the freeze-thaw cycle often causes changes in protein structure that affect protein function, as well as protein aggregation and precipitation.

Cryopreservation of sperm is essential for propagation of animals by artificial insemination, in human fertility treatments, and in preservation of endangered species. Current methods typically involve an initial slow cooling over dry ice ($T_v=195$ K) followed by more rapid cooling in liquid nitrogen to $T=77$ K. Sperm survival rates and especially fertilization rates after cryopreservation and thawing are highly variable and often extremely poor.

Cryopreservation is also crucial to protein crystallography, by which the molecular structure of proteins is determined. Protein and virus crystals are easily damaged by the X-rays used to measure their structures. This damage is greatly reduced by cooling the crystals to $T=120$ K or below. Diffusion of hydroxyl radicals, hydrogen radicals and other reactive species created by X-ray absorption is then limited, reducing their ability to attack the protein. Since these crystals contain large amounts of water, the frozen water provides a rigid framework that limits molecular motions in response to damage. Current methods used for cryoprotection involve soaking the crystals in cryoprotective agents and then cooling by inserting the crystal into a cold gas stream or plunging it into liquid nitrogen or propane. These methods damage the crystals, reducing the accuracy and detail of the molecular structure that can be obtained from X-ray diffraction measurements on them.

Common cooling agents used in cryopreservation to remove heat energy from samples and maintain them at low temperatures include dry ice ($T_v=195$ K); closed cycle cryogenic refrigerators ($T\approx 195$ K); cold gas streams at $T\sim 100$ K (nitrogen) or $T\sim 20$ K (helium); liquid nitrogen at its boiling point (Tv=77 K); hydrocarbons such as propane and ethane at temperatures just above their melting points ($T_m=90$ K and 83 K, respectively); and cryogenic refrigerants (chlorofluorocarbons (CFCs) and their modern replacements) that remain liquid below T=200 K. Liquids generally provide more efficient heat transfer and cooling than gases. Liquids having a large difference between their melting temperature and boiling temperature (such as propane ($T_v=184$ K, $\Delta T=94$ K) and ethane ($T_v=231$ K, $\Delta T=148$ K) and held just above their melting temperature can absorb more heat from a sample before vaporizing, than, e.g., nitrogen ($T_m=63$ K, $\Delta T=14$ K). Vapor evolved around a warm sample when it is plunged into the liquid insulates the sample from the liquid, reducing cooling rates; liquids like propane and ethane reduce the amount of vapor evolved and generally give larger heat transfer rates. For liquid samples, the gas evolution problem can be eliminated by freezing on a cold metal surface, but cooling on metal surfaces is less effective and/or damaging for protein crystals, cells and tissues.

Protein solutions, protein crystals, cells and tissues all contain large amounts of water, and so both the final sample temperature and the cooling rate to that temperature are important in determining the properties of the frozen sample and the success of cryopreservation. If water is cooled slowly, it will form crystalline (usually hexagonal) ice. The growth of ice crystals as the water freezes may puncture cell walls, rupture protein crystal lattices, and cause other damage to biological samples. If water is cooled rapidly below its glass transition temperature $T_g\approx 136$ K, crystalline ice formation can be avoided and the water will instead form an amorphous, vitreous or glassy state.

Pure water can only be vitrified with cooling rates approaching $10^6$ K/s, which are only achievable for samples with very small volumes ($<10^{-6}$ microliters) and with very large surface area-to-volume ratios. Cryoprotective agents (CPAs) like glycerol, ethylene glycol, dimethyl sulfoxide (DMSO), polyethelene glycols (PEGs), sugars and even proteins (at very high concentrations) inhibit crystalline ice formation and allow the vitreous phase to be obtained at higher temperatures and using smaller cooling rates. For sufficiently high CPA concentrations (e.g., 60% glycerol), the vitreous ice phase can be obtained even with very slow cooling, and at temperatures accessible using dry ice or −80° C. (193 K) refrigerators. Cryoprotective agents are thus widely used in cryopreservation of biological samples.

However, cryoprotective agents, especially at large concentrations, can cause osmotic shock to the sample leading to cell rupture or crystal cracking, changes in protein conformation, and other chemical and physical changes that degrade the sample before cooling and/or during subsequent warming. Thus, higher sample cooling rates are desirable to reduce the cryoprotective agent concentrations required to obtain vitreous ice.

Higher cooling rates are also desirable to maintain sample integrity and homogeneity during cooling, so as to capture and preserve the sample's initial native structure and function observed at, e.g., room or body temperature. Essentially all physical and chemical properties of the sample—including protein conformation and solubility, salt solubility, pH, and the activity of water—vary with temperature. Changes in these properties that occur during the time the sample is cooling can lead to precipitation of salt or protein, conformational heterogeneity of proteins, changes in membrane structure, and other problems so that the structure of the cryopreserved sample deviates from the initial structure. By cooling very rapidly, little time is allowed for the sample's constituents to respond to the changing temperature before all motion is frozen out. Rapid cooling may thus more accurately preserve the sample's native structure.

In protein cryocrystallography, crystals are cooled by insertion into a cold nitrogen gas stream at T≈100 K or by plunging into liquid nitrogen at its boiling point or liquid propane just above its melting point. Reported cooling rates are ~300-1500 K/s, so that the time for the crystal to cool from 273 K to 120 K is of order 0.1 to 1 s. Even when substantial concentrations of cryoprotectants (e.g., 30% glycerol) are used, these modest cooling rates result in substantial crystal damage as evident from X-ray diffraction measurements. This damage is a major factor limiting the quality of the resulting molecular structure. In at least some cases, the frozen protein structure differs in important ways from the room-temperature, biologically relevant structure. These modest cooling rates achieved in protein crystallography are still extremely large compared with those in standard protocols for cryopreservation of protein solutions, cells (e.g., sperm) and tissues, which are typically in the range of 0.1 to 10 K/s.

The fastest reported cooling rates of biological samples have been achieved in the field of cryoelectron microscopy. By plunging ~0.1 micron thick samples (produced by microtoming) supported on thin metal grids into liquid ethane at high speeds (~5 m/s), cooling rates up to roughly 300,000 K/s can be achieved. The Vitrobot, sold by FEI in Germany, is the most advanced commercial device for freezing samples for cryoelectron microscopy. Protein crystals, cells and tissues all have much larger dimensions and much smaller surface-to-volume ratios than the ultra-thin electron-transmissive samples used in cryoelectron microscopy. They cannot survive such high speed impacts with liquid cryogens, and the splashing when they (and their sample holders) impact the liquid cryogen is problematic.

The fastest cooling of water-containing liquid samples has been achieved either by shooting very small ($10^{-5}$ microliter) drops into vacuum, which then cool by evaporation, or by spraying small drops in vacuum onto cold metal surfaces. These methods can both be used to vitrify pure water, without added cryoprotective agents. The need for sending samples through vacuum (or low pressures) complicates cooling apparatus and protocols, and the evaporation and resulting dehydration of samples required for evaporative cooling may not accurately preserve the native sample structure. Evaporative cooling in vacuum is more effective than cooling in liquids or on solids only for very small samples ($10^{-5}$ microliter). Consequently, exposure of larger samples to vacuum or reduced pressures prior to or during a plunge into a cold liquid can cause slower cooling and more cooling related damage than when samples move through gas at atmospheric pressure (whose high thermal conductance and thermal mass minimizes sample cooling even the presence of evaporation.)

The inventors have investigated cooling by immersion (plunging) in liquid nitrogen (at $T_v$=77 K) and liquid propane (at T just above $T_m$=90 K) of drops of mixtures of water and common cryoprotective agents as a function of the drop volume. Drops with smaller volumes have larger surface-to-volume ratios and are thus expected to cool at higher rates. Smaller drops should then require smaller concentrations of cryoprotective agents in order for them to cool into the vitreous ice phase.

For a given CPA and for sample plunge speeds into the liquid of roughly 0.5 m/s, the minimum required cryoprotectant (e.g., glycerol) concentration was found to decrease with decreasing sample volume, as expected, for volumes above 0.1 microliters. But contrary to expectations, as the drop volume was decreased below 0.1 microliters, the minimum required cryoprotectant concentration remained roughly constant and large (roughly 28% w/v for glycerol). When drops were placed on an ultra-thin copper foil cup and then the bottom of the cup was plunged into contact with liquid nitrogen, the cryoprotectant concentration to achieve vitrification decreased monotonically with drop volume down to the smallest volumes examined ($10^{-4}$ microliters). This indicated that the saturation in cryoprotective agent concentration observed when drops were directly plunged into the cryogen was due to a saturation of the cooling rate with volume below 0.1 microliters (at that plunge speed). Since protein crystals used in molecular structure determinations by X-ray crystallography have volumes of $10^{-2}$ to $10^{-7}$ microliters, this saturation in cooling rate in conventional plunge cooling explained why smaller crystals have not, until now, shown significantly less damage on cooling, significantly better diffraction quality or required significantly less cryoprotectants than larger crystals.

SUMMARY OF THE INVENTION

The inventors have identified the reason for the small-volume saturation of sample cooling rate. The cold surface of a liquid cryogen (or of a solid cooled to cryogenic temperatures) cools the gas immediately above it. Consequently, there is a layer of cold gas of finite thickness. This thickness can be quantified as the distance above the surface at which the gas temperature rises, for example, by 70% of the difference between the liquid surface temperature and the gas temperature far from the surface, or to water's glass transition temperature, or to water's homogeneous nucleation temperature, or to its melting temperature.

A large volume (large thermal mass) sample can traverse this cold gas layer with little decrease in its temperature. In this case, nearly all cooling occurs in the liquid, and the cooling rate (time) is determined by heat transfer within the liquid.

However, a sufficiently small volume sample will cool rapidly in the gas layer, and its temperature at a given height above the surface will be close to that of the gas at that height. In this case, nearly all the cooling will occur in the gas layer, with the sample reaching the liquid (or solid) surface temperature just above the surface. The cooling rate will then be determined by the time it takes the sample to traverse the cold gas layer. The cooling time will be roughly given by the ratio of the cold gas layer thickness to the speed with which the sample traverses it. Consequently, if the plunge speed is held constant, the cooling rates of sufficiently small samples will be roughly independent of sample volume. For aqueous solutions containing cryoprotective agents, the minimum cryoprotectant concentration to achieve vitrification should then be independent of sample volume.

The experiments of the inventors show that for sample plunge speeds of roughly 0.5 m/s, the cross-over between these large and small volume cooling regimes occurs at a surprisingly large sample volume of roughly 0.1 microliters. This is one to six orders of magnitude larger than the sizes of crystals cooled in protein crystallography, and five orders of magnitude larger than the size of typical cells.

One way to increase the cooling rate of small samples is to increase the sample's plunge speed through the cold gas layer. Practical limits on plunge speeds into liquid cryogens are set by maximum sample accelerations and decelerations in a compact device; by splashing of the liquid cryogen as the sample enters its surface; and by sample deformations, damage and slippage relative to a sample holder caused by the accelerations and impact. State of the art commercial devices used to freeze samples for cryoelectron microscopy provide an increase in plunge velocity of only roughly a factor of 10 over what is readily achievable by hand (0.5 m/s), and thus increase cooling rates for small samples by a similar factor. Large plunge velocities are even more impractical when cooling is to occur on a solid surface. Thus, a need therefore remains for a technique for reducing the effects of the cold gas layer in plunge cooling of small samples.

The present invention addresses this need through provision of a method and devices for rapid cooling of small (10 microliter or smaller) samples to cryogenic temperatures which minimize the thickness of the cold gas layer that forms above the surfaces of liquid cryogens and of solids (e.g., copper) cooled to cryogenic temperatures, replacing this cold gas layer with gas at another, warmer and more uniform temperature at the same or similar pressure. In one preferred method, this is achieved by simply blowing the cold gas layer away. This greatly increases the temperature gradient in the gas immediately above the liquid or solid surface, so that when a small sample moves through the gas toward the surface, most cooling from its initial temperature will occur when it enters the liquid (or when it contacts the solid), not in the gas layer above it, even when it moves at modest speeds. As a result, heat transfer rates during cooling are greatly increased, and the time required to cool the sample between its initial temperature (for example, the ambient temperature far from the surface) and the liquid or solid temperature is dramatically reduced. Preliminary experiments suggest that this very simple method can yield cooling rates for sample speeds perpendicular to the surface of less than 1 m/s and at atmospheric pressure of up to 100,000 K/s, and that are comparable to the highest cooling rates reported for evaporative cooling of micrometer-size water drops in vacuum and of drops sprayed through vacuum onto cold metal surfaces. The modest sample speeds required reduce the chance of sample damage on impact with the liquid, allowing rapid cooling of fragile samples.

In a first preferred embodiment, the present invention overcomes the foregoing cooling effect by setting up a flow of warm, dry gas along or across the sample's path to the liquid or solid surface, thereby substantially reducing the thickness of the cold gas layer near the liquid or solid surface. Using modest $N_2$ gas flow speeds of a few meters per second or less, experiments have established that using this technique reduces the thickness of the gas layer as defined above from ~1 cm to <0.01 cm. By substantially removing the cold gas layer in this manner, measured cooling times for an 80 micron thermocouple plunged in liquid nitrogen (T=77 K) at a modest speed of 0.5 m/s drop from ~0.2 s to ~0.01 s, and cooling rates increase to 15,000 K/s. Reducing the sample volume to 10 micrometers (the size of single cells and the smallest protein crystals now used in protein crystallography) will decrease the cooling time to ~0.001 s. Consequently, cooling rates of order 100,000 K/s can be achieved by plunging through gas at atmospheric pressure, at very modest speeds, and into the least expensive and least dangerous liquid cryogen.

Experiments also establish that by removing the cold gas layer in this way, the minimum glycerol concentration required to achieve a vitrified sample during plunge cooling in liquid nitrogen decreases continuously with volume, to roughly 6% at a volume of $10^{-4}$ microliters, compared with roughly 30% in current practice. Extrapolation of the data to smaller volumes yields the same volume at zero glycerol concentration as has been obtained by evaporative cooling of water drops in vacuum and by spraying drops through vacuum onto a cold metal surface. Consequently, the improvements that cold gas layer removal provides are enormous, and approach the maximum cooling rates possible.

The cold gas layer can be removed by several mechanisms. In a first, a stream of warm, dry gas is projected along the sample's plunge path from a nozzle or other aperture held above the initial position of the sample. "Warm" here is relative to the temperature of the cold surface, and will typically be the initial sample temperature. For water-containing biological samples, the gas temperature should be above the sample's glass transition temperature and the homogeneous nucleation temperature for crystalline ice formation, and generally also above the melting temperature of the aqueous mixture within the sample. For pure water these temperatures are roughly 136 K, 233K and 273 K, respectively. "Dry" means free of water vapor, although it may also be desirable to eliminate other gases (e.g., oxygen and carbon dioxide) which have melting and/or boiling temperatures below that of the cold surface. All of these may condense on the sample and onto the cold surface, contaminating them. Nitrogen, argon and helium are thus good choices.

The gas stream may be coaxial with the plunge path or it may come at any angle to the plunge path, including along the cold surface. The gas nozzle or outlet may be held in a fixed position, or it may be attached to the vertical translation mechanism that holds the sample so that it moves with the sample. The size and shape of the nozzle, its distance above the surface of the liquid cryogen, and the gas flow velocity exiting it can be adjusted to produce the most efficient removal of the cold gas layer and the largest temperature gradient near surface of the liquid cryogen or solid surface.

The gas stream may be continuous, or it may be pulsed on using, e.g., a mechanically, pneumatically or electrically actuated valve just before the plunge and then turned off after the plunge. Pulsing the gas stream can minimize evaporation of liquid cryogen and, in the case of liquid cryogens held at temperatures well below their boiling temperatures (e.g., propane or ethane) or solids surfaces, minimize warming of the liquid or solid near the surface.

In a second mechanism, a continuous or intermittent stream of warm dry gas is flowed through a tube in which the sample resides, and through which it moves during plunging into the liquid cryogen (nitrogen, propane, ethane) or onto the solid surface. The tube may be held above the cold surface so that its walls remain warm. Gas venting at the lower end of the tube may be through apertures in the walls of the tube, or through the end of the tube. The tube should be of a material with low thermal mass and low thermal conductance like plastic or glass.

In a third mechanism, the liquid cryogen or cold surface may have an enclosed gas volume above it. The gas is replaced with warm dry gas immediately prior to the plunge. The sample may enter through a shutter that is closed while the volume is purged. The gas could be removed by pumping before introducing new gas immediately prior to the plunge.

A fourth mechanism raises the liquid cryogen to meet the sample, rather than plunging the sample into the cryogen, in a way that allows the cold gas above it to flow out of the way. However, this will generally be less effective in collapsing the cold gas layer to a minimum thickness than the methods described above.

In addition to the foregoing mechanisms, a thin shield can be placed immediately above the liquid cryogen or solid surface, and cover most or all of it. If it is of an insulating material and has integral radiation shielding (e.g., an aluminized mylar film), it can be used to reduce condensation and freezing of water vapor onto the cold surface between plunges. It can also reduce the exposed area and heat transfer, reducing evaporation of liquid cryogens. Reducing the exposed area may also reduce the native height of the cold gas layer, and also the flow speed and flow volume of the warm dry gas needed to remove it. A small shutter or aperture in the shield can be opened when the sample is plunged.

The foregoing apparatus will produce large increases in cooling rates compared with conventional plunge cooling in the presence of cold gas layers for samples with volumes below ten microliters (for slow plunge velocities) and below one microliter for common plunge velocities.

For biological or other dehydration- or air-sensitive samples, the apparatus may include a separate sample chamber, separated by a valve or shutter from the chamber or volume through which the sample is plunged. The environment (e.g., humidity, temperature and oxygen partial pressure) in the sample chamber can be adjusted so as to maintain or achieve desired sample properties prior to cooling.

The apparatus may also include mechanisms for capturing the sample after freezing and transferring it to a storage container. For example, when cooling is performed in liquid cryogens, it may contain cryovials such as those sold by Hampton Research, into which the sample is inserted. It may contain a multiple sample carousel (e.g., made from metal) that is immersed in the cryogen, and into which samples are inserted. A mechanism for holding and translating these holders (or the sample) can also be included. For freezing on solid surfaces, a mechanism for scraping the sample off the surface and into a storage container could be included.

BRIEF DESCRIPTION OF THE DRAWINGS

The features and advantages of the present invention will become apparent from the following detailed description of a number of preferred embodiments thereof, taken in conjunction with the accompanying drawings which are briefly described as follows.

DETAILED DESCRIPTION OF THE PREFERRED EMBODIMENTS

Before a more detailed consideration of the various preferred embodiments of the present invention will be presented, the exponent and investigations conducted by the inventors which ultimately led to the creation of the present invention will be discussed.

Figure 1:
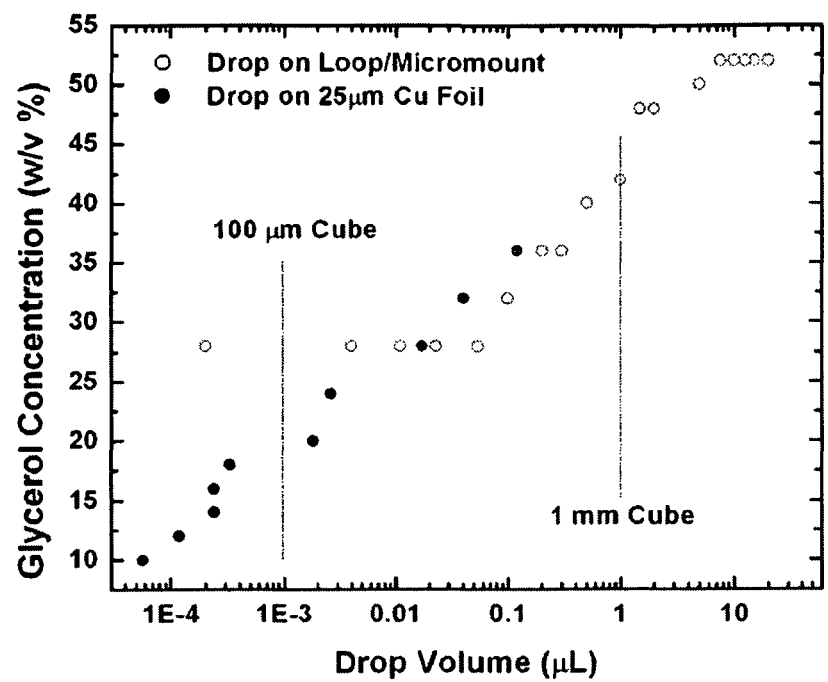
FIG. 1 is a graph of the minimum glycerol concentration required for vitrification of glycerol-water mixtures versus drop volume. Open circles are data collected by plunging drops held in tungsten wire loops (for volumes above 1 μl) or in microfabricated polyimide loops (below 1 μl) into liquid nitrogen at $T_v$=77 K without removing the cold gas layer. Solid circles represent data collected by spraying drops onto the bottom of a 25 μm thick copper cup and then plunging the bottom of the cup into liquid nitrogen. Vertical lines indicate corresponding linear dimensions of cubic samples.

First, the inventors have investigated flash cooling by immersion in liquid nitrogen and liquid propane of common water-cryoprotectant mixtures as a function of the volume cooled. The liquid drop samples were cooled by plunging them from air into a Dewar flask of liquid nitrogen or propane, the same method that is used for flash cooling protein crystals for cryocrystallography. FIG. 1 shows the minimum glycerol concentration required to obtain a vitrified sample upon plunging into liquid nitrogen. Open circles are data collected by plunging drops held in tungsten wire loops (for volumes above 1 μl) or in microfabricated polyimide loops (below 1 μl) into liquid nitrogen at $T_v$=77 K without removing the cold gas layer. Solid circles represent data collected by spraying drops onto the bottom of a 25 μm thick copper cup and then plunging the bottom of the cup into liquid nitrogen. Vertical lines indicate corresponding linear dimensions of cubic samples.

The data for direct plunging of drops in liquid nitrogen show that the glycerol concentration and therefore the sample cooling rate saturates for volumes below 0.1 μL, indicating that there is no advantage (reduction in glycerol concentration) to using smaller volumes. A similar saturation is observed when samples are cooled in liquid propane held at temperatures just above its melting point. In contrast, the data obtained using the copper foil cup do not show this saturation, even though the liquid nitrogen never touched the drops, and the cryoprotectant concentration decreases monotonically with decreasing volume. This indicates that smaller drops freeze much more quickly on the copper than when directly plunged into liquid nitrogen.

Figure 2:
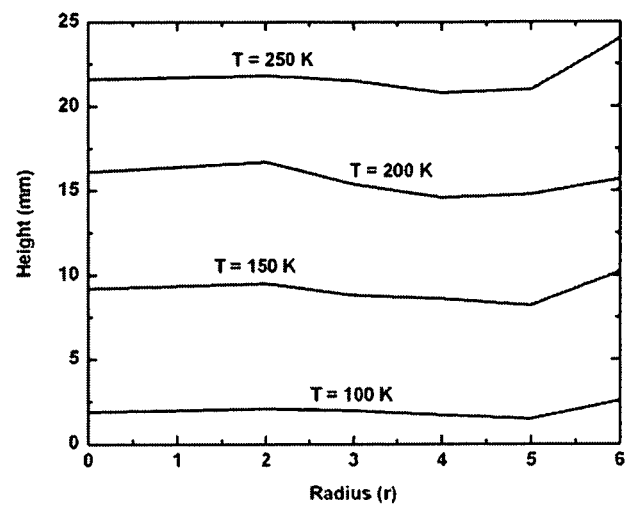
FIG. 2 is a graph of equal-temperature contours measured above a standard 20 cm diameter wide-mouth Dewar flask used in plunge cooling protein crystals and cells that is filled with liquid nitrogen at $T_v$=77 K to within 4 cm of the brim of the dewar.

FIG. 2 is a graph of equal-temperature contours measured in the gas above a standard 20 cm diameter wide-mouth Dewar flask used in plunge cooling protein crystals and cells, and that is filled with liquid nitrogen to within 4 cm of the brim of the dewar. The measurements were performed on an open laboratory bench in a room with normal ventilation. For liquid nitrogen, the temperature in the gas falls below water's melting temperature $T_m$=273 K at roughly 2.5 cm above the liquid surface, below water's homogeneous nucleation temperature $T_h$=233 K roughly 2 cm above the liquid surface, and below water's glass transition temperature $T_{g,0}$=136 K roughly 0.7 cm above the liquid surface.

Figure 3:
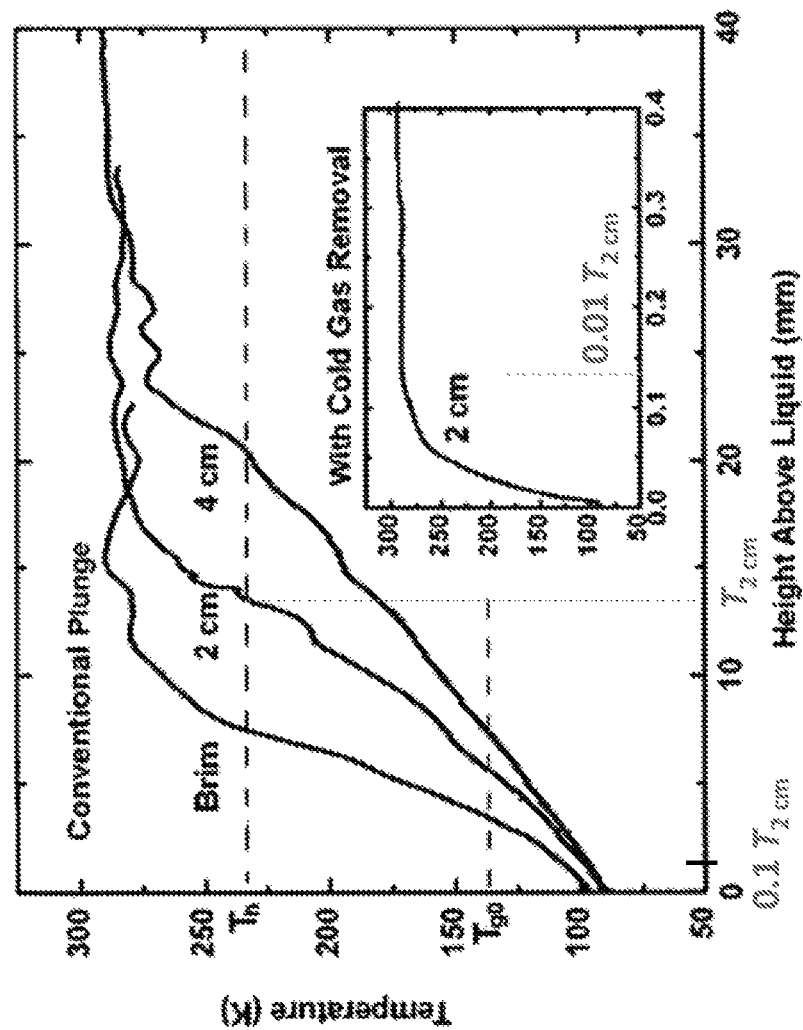
FIG. 3 is a graph of gas temperature as a function of height above liquid nitrogen held at $T_v$=77 K near the center of a 20 cm diameter dewar, for different liquid fill levels (measured in cm from the brim). The inset shows the gas temperature versus height above liquid nitrogen in the same dewar when dry nitrogen gas at T=293 K is blown along the thermocouple's path, as described in the present invention. $T_h$ and $T_{g0}$ denote pure water's homogeneous ice crystal nucleation temperature and its glass transition temperature, respectively.

FIG. 3 is a graph of gas temperature as a function of height above liquid nitrogen held at $T_v$=77 K near the center of a 20 cm diameter hemispherical dewar, for different liquid fill levels (measured in cm from the brim). The inset shows the gas temperature versus height above liquid nitrogen when dry nitrogen gas at T=293 K is blown along the thermocouple's path, as described in the present invention. Blowing at very modest gas velocities (a few m/s) reduces the thickness of the cold gas layer above the liquid (when filled to a depth of 4 cm below the brim) from ~2 cm to less than 100 µm, a reduction of more than two orders of magnitude.

Figure 4:
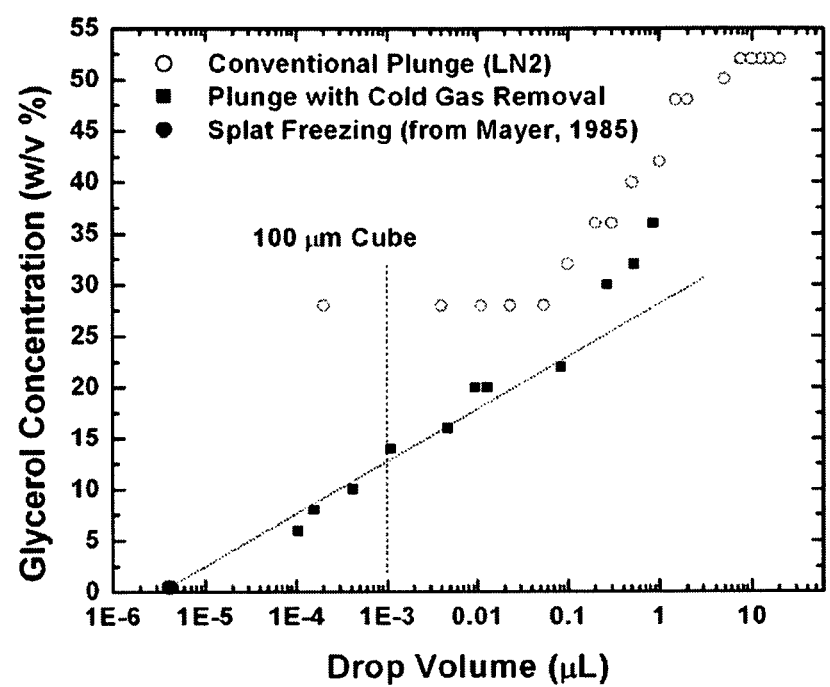
FIG. 4 is a graph showing minimum glycerol concentrations required for vitrification of water-glycerol mixtures versus sample volume. Open circles are the data of FIG. 1 for direct plunge into liquid nitrogen without cold gas layer removal. Solid squares are data collected for a direct plunge into liquid nitrogen using a dry nitrogen gas stream to remove the cold gas layer. The solid circle is a result from the prior art for vitrifying pure water by spraying small drops in vacuum onto a cold copper surface.

FIG. 4 shows the dramatic effect of reducing the gas layer thickness on small samples. FIG. 4 shows the minimum glycerol concentrations required for vitrification of water-glycerol mixtures versus sample volume. Open circles are the data of FIG. 1 for a direct plunge into liquid nitrogen without cold gas layer removal. Solid squares are data collected for a direct plunge into liquid nitrogen using a dry nitrogen gas stream to remove the cold gas layer. Cold gas layer removal eliminates the small-volume saturation of glycerol concentration and cooling rates below volumes of 0.1 µl, and the glycerol concentration decreases continuously to the smallest volume ($10^{-4}$ µl) measured. Without cold gas layer removal, the required concentration below 0.1 microliters saturates at 28% w/v. With cold gas layer removal, the required glycerol concentration decreases continuously with volume, to roughly 6% at a volume of 0.1 nl. Moreover, extrapolation of the data for plunge cooling with gas flow to smaller volumes yields the roughly same volume at zero glycerol concentration as has been obtained by evaporative cooling of pure water drops in vacuum and by spraying pure water drops in vacuum onto cold metal surfaces. Consequently, the improvements that cold gas layer removal provides are enormous, and approach what is theoretically possible.

Consequently, without cold gas layer removal, the cooling rate and minimum glycerol concentration saturate for sample volumes below 0.1 µl, a volume that is larger than, for example, almost all protein crystals used in X-ray crystallography and much larger than the size of single cells. By removing the cold gas layer, this saturation is eliminated, and cooling rates measured using 80 µm thermocouples can be increased from several hundred K/s to 15,000 K/s or more. Consequently, by removing the cold gas layer and using small volume samples, sample cooling rates in liquid nitrogen can be increased by two orders of magnitude or more, without the need to resort to more dangerous or expensive cooling agents like propane, or to exposing the sample to the dehydrating effects of vacuum.

Our invention is a series of apparatus for rapid cooling of small samples to low temperatures that dramatically reduces the thickness of the cold gas layer that forms above cold surfaces, producing a nearly abrupt transition from ambient (e.g., room) temperature to the temperature of the cold liquid or cold solid surface, so as to maximize the spatial gradient in temperature near the gas-liquid or gas-solid interface. In all cases, the objective is either to minimize the cold gas layer thickness along the path of the sample either by removing it or preventing it from forming in the first place. The apparatus consists of a mechanism for removing the cold gas layer above the liquid or solid or preventing it from forming, a mechanism for holding the sample, a mechanism for translating the sample relative to the cold liquid or solid, and either a container for the cold liquid, or a solid thermally conducting material that is cooled by a cold liquid or by a cryogenic refrigerator.

Figure 5:
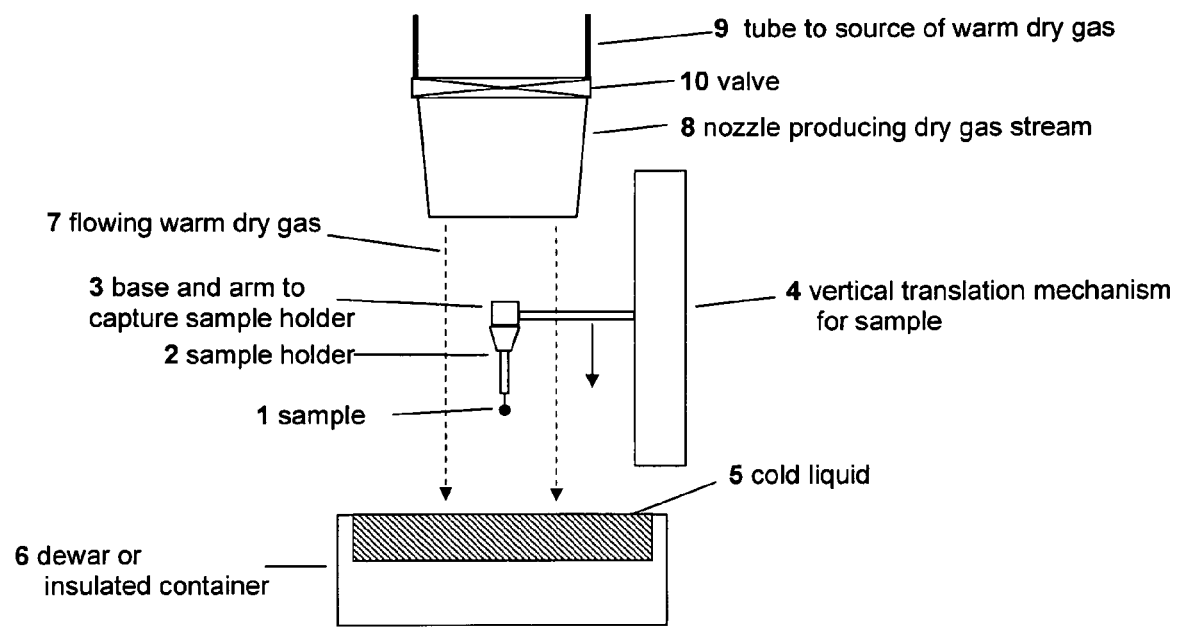
FIG. 5 is a schematic illustration of a first preferred embodiment for reducing or eliminating the cold gas layer adjacent the surface of a liquid cryogen, in which a gas stream nozzle coaxial with the sample plunge path supplies warm (e.g., room temperature) dry gas along the sample's plunge path above the liquid cryogen.

FIG. 5 shows one preferred implementation of the present invention for cooling to temperatures below 200 K (and typically below $T_{go}$=136 K) in liquids such as liquid nitrogen, liquid propane, liquid ethane, or CFC-like refrigerants with appropriately low melting temperatures. The sample 1 and its holder 2 are held to a base 3 by, e.g., a magnet, an electromagnet, a screw or twist-lock connection, and a positive action jawed gripper (perhaps electrically or pneumatically actuated).

This base is attached to a vertical translation mechanism 4. The vertical translation mechanism can be driven by, e.g., gravity (e.g., simple free fall along a guiding rod, a lever (which can produce sample accelerations greater than 10 m/s², or a guillotine-like mechanism), by a solenoid, by a linear or stepper motor (e.g., along a rotating screw), by a nanomotion motor, by compressed gas (via a piston), and by a mechanical mechanism that couples a spinning weight with an electric clutch to a linear translation stage. It could also be translated using a multiple axis robotic arm/manipulator The motion can be tailored in each of these mechanisms to provide limited acceleration magnitudes during acceleration from rest and deceleration to a stop in the liquid cryogen. This will prevent the sample from sliding off the sample holder during initial acceleration, which becomes less of a concern as the sample mass becomes smaller. The vertical translation mechanism moves the sample through warm gas (e.g., air at ambient temperature and pressure) to the cold liquid 5 which is held in a dewar or other thermally insulating container 6.

The cold gas layer can be removed by several mechanisms. In FIG. 5, a stream of warm (e.g., ambient temperature) dry gas (e.g., nitrogen) 7 is projected along the sample's plunge path from a nozzle 8 or other aperture held above the initial position of the sample. The nozzle is connected by a tube or hose 9 to source of the gas (e.g., a compressed gas cylinder, boil-off from liquid nitrogen, a nitrogen generator). The nozzle may be held in a fixed position, or it may be attached to the vertical translation mechanism that holds the sample so that it moves with the sample. The size and shape of the nozzle, its distance above the surface of the liquid cryogen, and the gas flow velocity exiting it can be adjusted to produce the most efficient removal of the cold gas layer and the largest temperature gradient at the surface the liquid cryogen. Preliminary experiments indicate that very modest gas flows (a few m/s or less) are sufficient to collapse the cold gas layer thickness to below 100 µm. The gas stream may be continuous, or it may be pulsed on using, e.g., a mechanically, pneumatically or electrically actuated valve 10 just before the plunge, to minimize evaporation of liquid cryogen.

Figure 6:
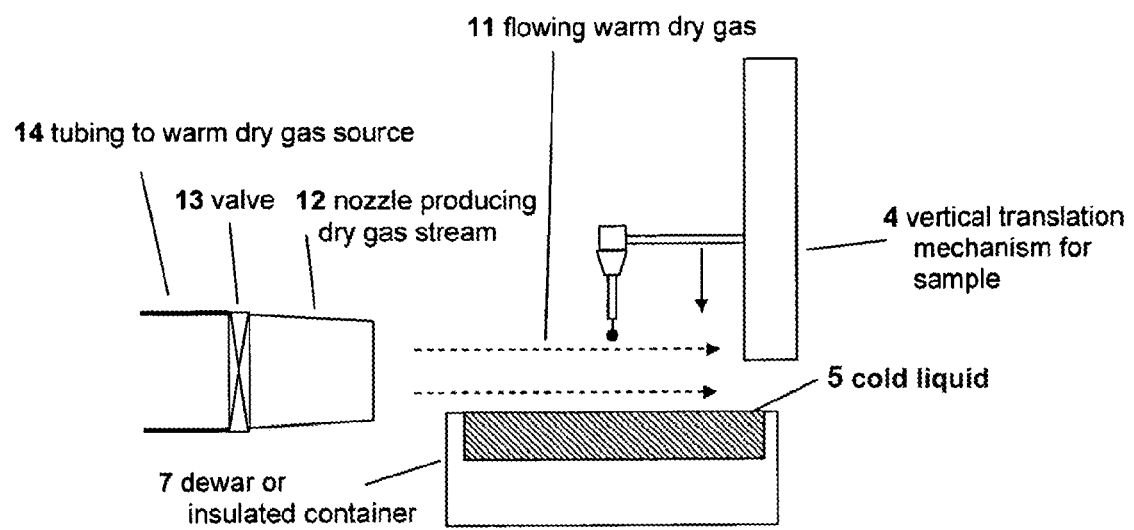
FIG. 6 shows a second preferred embodiment in which the gas stream is directed along the surface.

The gas stream may be coaxial with the plunge path, as shown in FIG. 5, or it may come at an angle (anywhere from 0 to 90 degrees) from the plunge path. FIG. 6 shows an alternative preferred embodiment in which the warm dry gas 11 flows through a nozzle 12 and valve 13 from a tube connected to the gas source 14, and flows horizontally along the surface of the cold liquid. The distance of exposed liquid surface over which the gas flows can be minimized to reduce heating and evaporation of the liquid. This approach reduces the thickness of moving gas through which the sample moves during the plunge into the liquid, and thus reduces additional evaporation from the sample caused by the gas motion (provided that the plunge speed relative to the ambient gas is small compared with the gas flow speed.)

Figure 7:
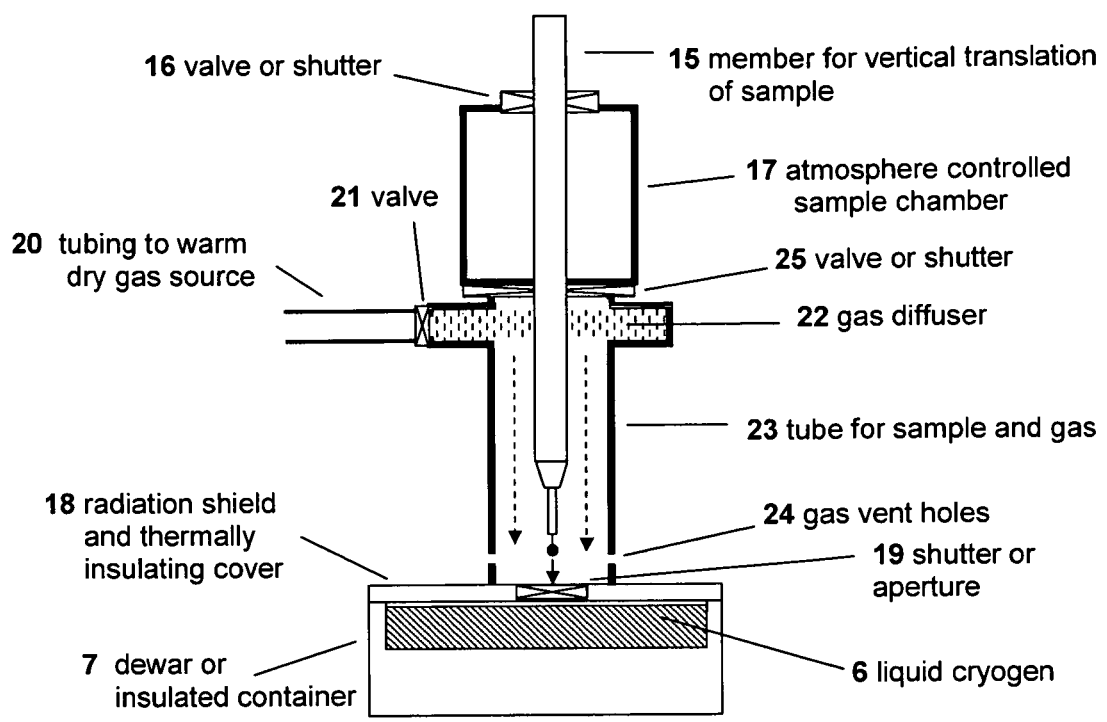
FIG. 7 shows a variant of the embodiment of FIG. 5 in which the sample is initially held in an environment-controlled chamber, and then translated through a second chamber that is used to remove the cold gas layer to the liquid cryogen.

FIG. 7 shows another embodiment of the present invention based on that in FIG. 5. In this embodiment, the sample and its holder are attached to a vertical member 15 that vertically translates the sample. The sample is first attached to member 15 and then translated through a shutter or valve 16 into an environment controlled chamber 17, which maintains, e.g., a desired temperature, relative humidity or oxygen partial pressure so as to maintain the sample's integrity prior to cooling. The cold liquid is covered by a thermally insulating and radiation shielding cover 18, which has a shutter or aperture 19 through which the sample may pass. The shielding cover 18 can reduce condensation and freezing of water vapor and other gases that liquify and/or freeze at temperatures above that of the cold liquid onto the surface of the liquid. The shield also reduces heat transfer to, warming and evaporation of the cold liquid, and reduces radiative cooling of the sample prior to its plunge. Prior to plunging the sample, the cold gas that has formed above the cold liquid is removed by flowing warm dry gas from its source through tube 20, valve 21 and diffuser 22 (to produce a more nearly uniform flow) through the tube 23 and across the liquid surface, exiting either at the bottom of the tube and/or through vent holes 24 in its side. Once the cold gas has been removed in this way, the valve or shutter 25 is opened and the sample plunged through tube 20 and into the cold liquid. The tube 20 should be held above the surface of the liquid cryogen so that its walls remain warm, and should be of a material with low thermal mass and low thermal conductance like plastic or glass.

Figure 8:
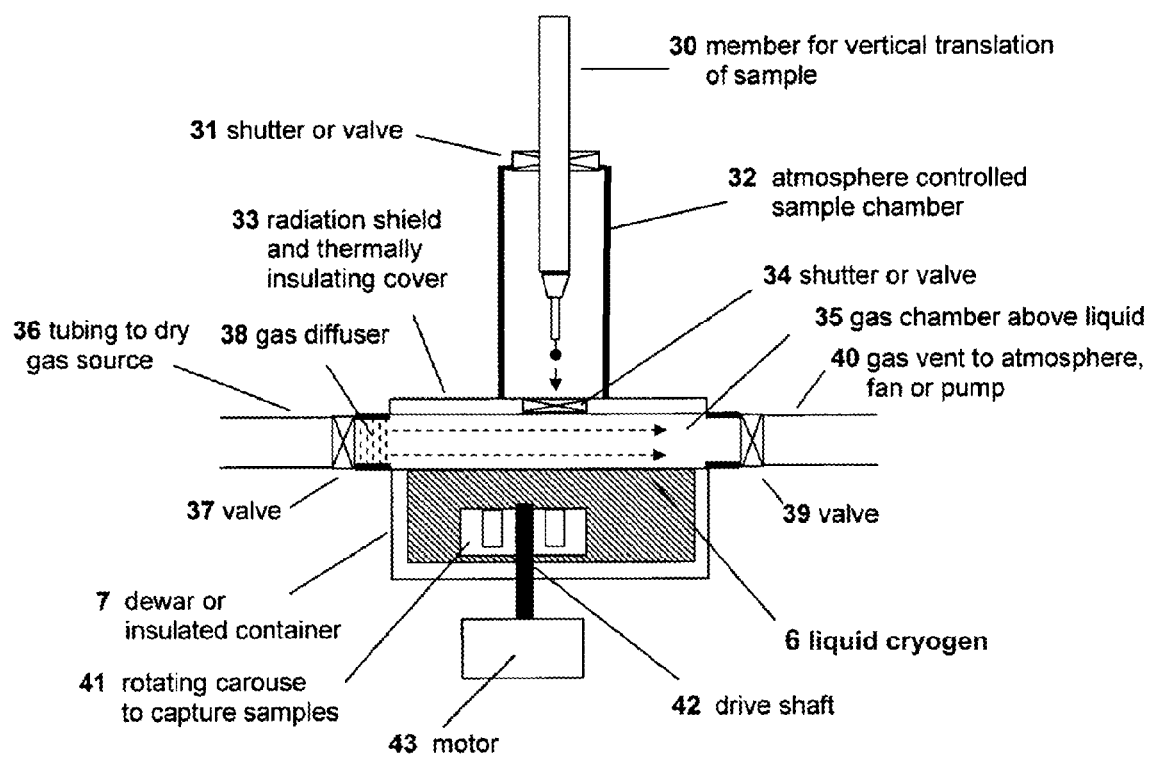
FIG. 8 shows a variant of the embodiment of FIG. 6, including an environment controlled sample chamber, a chamber that allows removal of the cold gas layer, and a rotating holder to capture samples after they have been frozen.

FIG. 8 shows another embodiment of the present invention based on the embodiment in FIG. 6. The sample and holder are again mounted on a vertical translation member 30 and translated though a shutter or valve 31 into an environment controlled chamber 32. The cold liquid is covered by a thermally insulating and radiation shielding cover 33, which has a shutter or valve 34 through which the sample may pass. In this case, this shield forms the top of an enclosed chamber 35 above the cold liquid. Prior to plunging the sample, the cold gas layer that forms above the cold liquid is removed by flowing warm dry gas from its source through tube 36, valve 37 and diffuser 38, over the surface of the cold liquid, and out through valve 39 and the vent 40. The gas removal may be facilitated by a fan or pump or piston connected to the vent. Before opening valve 37, the gas in chamber 35 may be pumped out, and then replaced with warm gas immediately prior to the plunge. Once the chamber 35 has been purged with warm gas, the sample is plunged through valve 34 and chamber 35 into the cold liquid. A rotating carousel or holder 41 connected by a drive shaft 42 or magnetic coupling to a motor 43 or other mechanism may be used to capture and hold the samples after they are frozen, and could allow many samples to be conveniently stored and/or removed.

In all of the embodiments discussed so far, the cold gas layer thickness is reduced by flowing warm gas relative to the surface of the cold liquid, which is stationary in the frame of the apparatus. The cold gas layer may also be removed by moving the cold liquid relative to the surrounding gas which is stationary relative to the frame of the apparatus, instead of moving the gas. For example, the liquid cryogen may be raised to meet the sample, rather than plunging the sample into the cryogen, in a way that allows the cold gas above it to flow out of the way. The container in which the liquid is held may be raised, or the cold liquid may be projected using pressure produced by a pump or gravity either upwards toward the sample (like a fountain) or through a horizontal trough. The sample can then be plunged into the fountain or trough shortly after the cold liquid flow has been established, and before a cold gas layer of significant thickness can form.

The initial thickness of the cold gas layer can be minimized by placing a thermally insulating solid material immediately above the liquid surface, so that the gas-filled gap between liquid and insulating solid is very small. A hinged or separately mounted aperture disk in this insulating layer may be translated or rotated out of the way and, if necessary, warm gas flowed over the exposed liquid surface, immediately prior to plunging the sample.

These apparatus will produce large increases in cooling rates compared with conventional plunge cooling in the presence of cold gas layers for samples with volumes below ten microliters and especially below one microliter. The increases in cooling rate will be especially large for small sample velocities relative to the liquid, which are less likely to damage fragile biological samples. And they can be achieved while keeping the sample at ambient temperature and pressure up to the moment that they enter the liquid, minimizing evaporation and evaporative cooling.

The embodiments of the present invention shown in FIGS. 5-8 all use a cold liquid as the cooling agent, but could also use a cold solid surface. This could be of a highly thermally conductive material like copper, and could be cooled either by contact with a cold liquid like liquid nitrogen, or using a closed cycle cryogenic refrigerator. For protein crystals, cells and tissues, the force of impact with the solid surface may be damaging, and removing frozen samples from the cold solid surface may also be difficult. However, for liquid samples such as protein solutions, cold solid surfaces (e.g., formed into cups) may provide both rapid cooling and convenient storage and handling.

Figure 9:
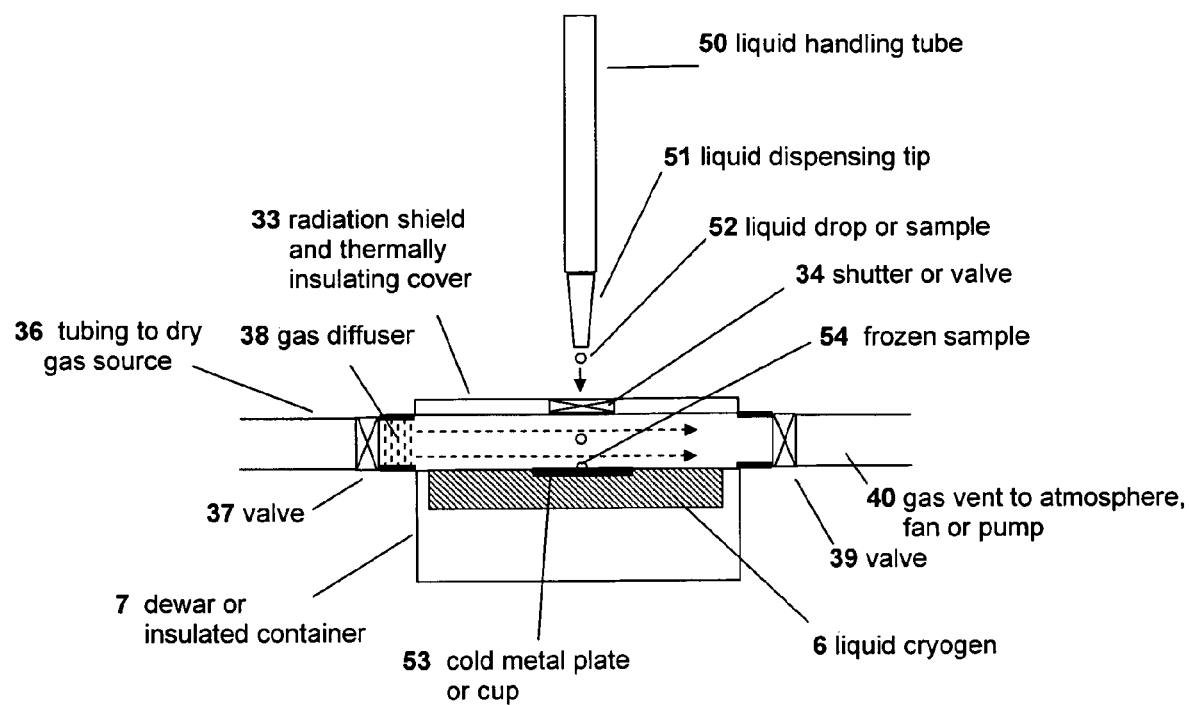
FIG. 9 shows a third preferred embodiment for rapidly cooling liquid samples or samples contained in liquid drops on cold metal plates or cups. The cold gas above the plate is removed immediately prior to sample dispensing, and then the sample is projected towards the surface of the cold plate, onto which it freezes.

FIG. 9 shows an embodiment of the present invention for freezing liquid samples. The liquid flows through handling tube 50 and the dispensing tip 51, which preferably generates a series of small volume (less than 1 µl) drops 52. These drops then fall (or are projected by pressure, electrostatic forces, or downward motion of the dispensing tip) through shutter 34 and onto the cold metal plate or cup 53, producing frozen drops 54 on its surface. The metal or cup may be rotated and translated so that successive drops land on exposed metal surface. In this case, the gas flow may be turned off immediately prior to drop dispensing so that the drops are not carried away by the cold gas. Alternatively, the distance between the solid surface and the insulating layer can be reduced, so that the vertical distance the drop falls—and thus the time and distance that it is deflected by the moving gas—is minimized.

As with cooling in cold liquids, the key is to set up relative motion of the cold surface and the gas above it. Thus, instead of flowing gas across a stationary solid surface, the solid surface can be quickly rotated or translated to a new position immediately prior to the plunge, leaving the cold gas behind. For example, the cold surface could have the form of a thin metal blade that is rotated or translated in the plane of the blade. Multiple thin blades could then be used to freeze and store multiple samples or large volumes of a given sample.

Although the invention has been disclosed in terms of a number of preferred embodiments and variations thereon, it will be understood that numerous other variations and modifications could be made thereto without departing from the scope of the invention as defined in the following claims.

What is claimed is:

1. A system for rapidly cooling a small sample having a volume equal to or less than 10 microliters and an initial, non-freezing temperature to a temperature of a cryogenic medium that it will contact, comprising:

a non-flowing, cryogenic medium, characterized by a stationary cold gas layer having a thickness, T, immediately adjacent a surface of the non-flowing cryogenic medium, where T is the distance above the surface of the non-flowing, cryogenic medium at which the gas temperature rises by at least 70% of the difference between the cryogenic medium surface temperature and the gas temperature at ambient, or to water's glass transition temperature, or to water's homogeneous nucleation temperature, or to a melting temperature of the sample; and a source that provides a forced volume of warm, dry air actively disposed into the cold gas layer prior to contact of the small sample with the cryogenic medium configured to actively reducing the thickness, T, to a layer having a thickness equal to or less than 0.1T immediately adjacent the surface of the non-flowing cryogenic medium, wherein 'warm' means one of: a) the initial temperature of the small sample, where the initial temperature of the small sample is higher than the gas temperature over the thickness, T, and b) for a water-containing biological sample, greater than the sample's glass temperature and the homogeneous nucleation temperature for crystalline ice formation.

2. The system of claim 1, wherein the source that provides the forced volume of warm, dry air is configured to actively reduce the thickness, T, to the layer having the thickness equal to or less than 0.01T immediately adjacent the surface of the non-flowing cryogenic medium.

3. The system of claim 1, further wherein the forced volume of warm, dry air actively disposed in the cold gas layer has a controllable velocity relative to the stationary cold gas layer.

4. The system of claim 1, wherein the source that provides the forced volume of warm, dry air has an air exit direction that is oriented at an angle, $\theta$, to the surface of the non-flowing cryogenic medium, where $0<\theta<180$ degrees.

5. The system of claim 1, wherein the non-flowing, cryogenic medium is a cryogenic liquid.

6. The system of claim 5, wherein the cryogenic liquid is one of nitrogen, propane, and ethane.

7. The system of claim 1, wherein the non-flowing, cryogenic medium is a cryogenically cooled solid.

8. The system of claim 1, wherein the source that provides the forced volume of warm, dry air includes at least one of a nozzle, a valve, a piston/cylinder, and a fan.

9. The system of claim 1, wherein the source that provides the forced volume of warm, dry air is translatable with respect to the non-flowing, cryogenic medium.

10. The system of claim 1, further comprising a sample holder configured to hold the sample at an initial position above the cold gas layer having the thickness T.

11. The system of claim 10, further comprising a tube in which the source that provides the forced volume of warm, dry air and the sample holder are disposed.

12. The system of claim 1, wherein the source that provides the forced volume of warm, dry air is a pulsed source of the forced volume of warm, dry air.

13. A method for rapidly cooling of a small sample having a volume equal to or less than 10 microliters and an initial, non-freezing temperature to a temperature of a cryogenic medium that it will contact, comprising the steps of:

providing a non-flowing, cryogenic medium, characterized by a stationary cold gas layer having a thickness, T, immediately adjacent a surface of the non-flowing cryogenic medium, where T is the distance above the surface of the non-flowing, cryogenic medium at which the gas temperature rises by at least 70% of the difference between the cryogenic medium surface temperature and the gas temperature at ambient, or to water's glass transition temperature, or to water's homogeneous nucleation temperature, or to a melting temperature of the sample; and reducing the thickness, T, to a layer having a thickness equal to or less than 0.1T immediately adjacent the surface of the non-flowing cryogenic medium by actively directing a forced volume of warm, dry air into the cold gas layer prior to cooling of the sample, wherein 'warm' means one of: a) the initial sample temperature and b) for a water-containing biological sample, greater than the sample's glass temperature and the homogeneous nucleation temperature for crystalline ice formation.

14. The method of claim 13, further comprising actively reducing the thickness, T, to the layer having the thickness equal to or less than 0.01T immediately adjacent the surface of the non-flowing cryogenic medium.

15. The method of claim 13, further comprising controlling the velocity of the forced volume of warm, dry air into the cold gas layer.

16. The method of claim 13, further comprising directing the forced volume of warm, dry air into the cold gas layer at an angle, $\theta$, to the surface of the nonflowing cryogenic medium, where $0<\theta<180$ degrees.

17. The method of claim 13, wherein the step of providing the nonflowing, cryogenic medium further comprises providing a non-flowing, cryogenic liquid.

18. The method of claim 17, further comprising providing one of nitrogen, propane, and ethane.

19. The method of claim 13, wherein the step of providing the nonflowing, cryogenic medium further comprises providing a cryogenically cooled solid.

20. The method of claim 13, further comprising blowing the warm, dry air into the cold gas layer.

21. The method of claim 20, further comprising intermittently blowing the warm, dry air into the cold gas layer.

22. The method of claim 13, further comprising holding the sample at an initial position above the cold gas layer having the thickness T prior to reducing the thickness, T, by actively directing the forced volume of warm, dry air into the cold gas layer, and automatically contacting the sample with the non-flowing, cryogenic medium subsequent to reducing the thickness, T, by actively directing the forced volume of warm, dry air into the cold gas layer.

* * * * *